(12) United States Patent
Fleury et al.

(10) Patent No.: US 6,229,312 B1
(45) Date of Patent: May 8, 2001

(54) METHOD AND DEVICE FOR FAST MEASUREMENT OF THE RESISTIVITY INDEX OF SOLID SAMPLES SUCH AS ROCKS

(75) Inventors: Marc Fleury, La Celle; Françoise Deflandre, Saint Cloud, both of (FR)

(73) Assignee: Institut Francais du Petrole, Cedex (FR)

( * ) Notice: Subject to any disclaimer, the term of this patent is extended or adjusted under 35 U.S.C. 154(b) by 0 days.

(21) Appl. No.: 09/359,765

(22) Filed: Jul. 22, 1999

(30) Foreign Application Priority Data

Jul. 24, 1998 (FR) .................................................. 98 09542

(51) Int. Cl.$^7$ .............................. G01V 3/00; G01R 27/08
(52) U.S. Cl. ........................ 324/376; 324/698; 250/255; 73/152.09; 73/38
(58) Field of Search ........................... 324/376, 64, 698; 73/38, 152.09, 37, 19.05, 153.11; 166/250.02; 175/44; 250/255

(56) References Cited

U.S. PATENT DOCUMENTS 5,164,672   11/1992   Gilliland et al. ...................... 324/376
5,679,885  * 10/1997   Lenormand et al. ...................... 73/38

FOREIGN PATENT DOCUMENTS 4208953   9/1992   (DE) ............................... G01N/27/04
2724460   3/1996   (FR) ............................... G01N/33/24

* cited by examiner

*Primary Examiner*—Hezron Williams
*Assistant Examiner*—Anthony Jolly
(74) *Attorney, Agent, or Firm*—Antonelli, Terry, Stout & Kraus, LLP

(57) ABSTRACT

Method and device for measuring the resistivity index curve (Ir) of a solid sample such as a geologic sample independently of the capillary pressure curve (Pc). Multi-frequency complex impedance measurements are carried out for a sample subjected to a radial confining pressure, during operations of drainage or imbibition of a first, initially saturating fluid, through a semipermeable membrane permeable to this first fluid, placed at a first end of a containment cell, by injection of a second fluid under pressure at the opposite end thereof. One or more injection pressure stages are applied and the continuous variations of the resistivity index (Ir) as a function of the average saturation (Sw) variation are measured without waiting for the capillary equilibria to be reached. Electrodes pressed against the sample on the periphery thereof are used, these electrodes having a given longitudinal extension in relation to the length of the sample and being connected to an impedance meter. An electric current is applied through the sample and the resulting electric potential difference variations are detected. Index Ir can be measured during a relatively short period of time, from a few hours to a few days according to the permeability of the core sample. The method and device can be applied for underground zone survey for example.

13 Claims, 4 Drawing Sheets

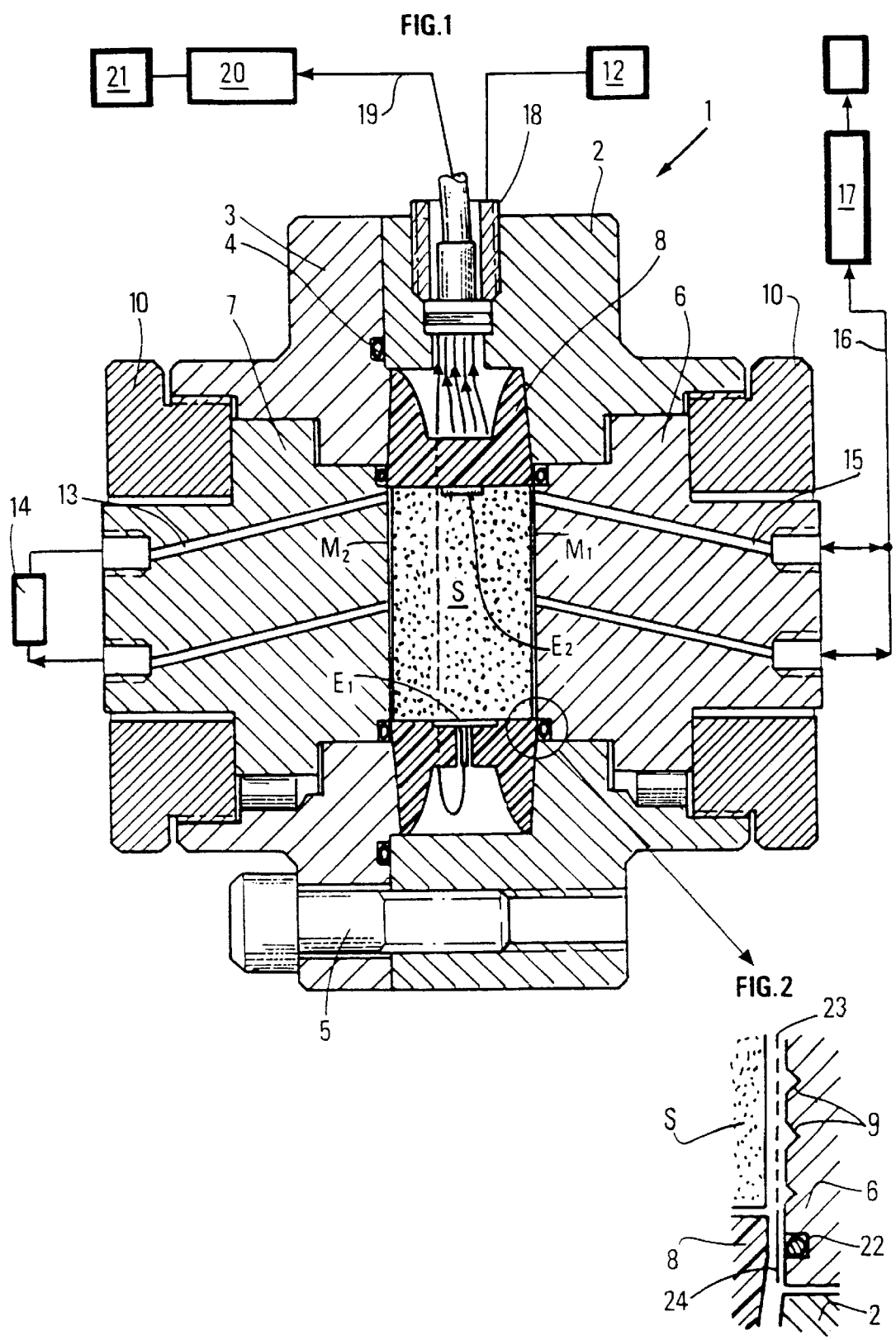

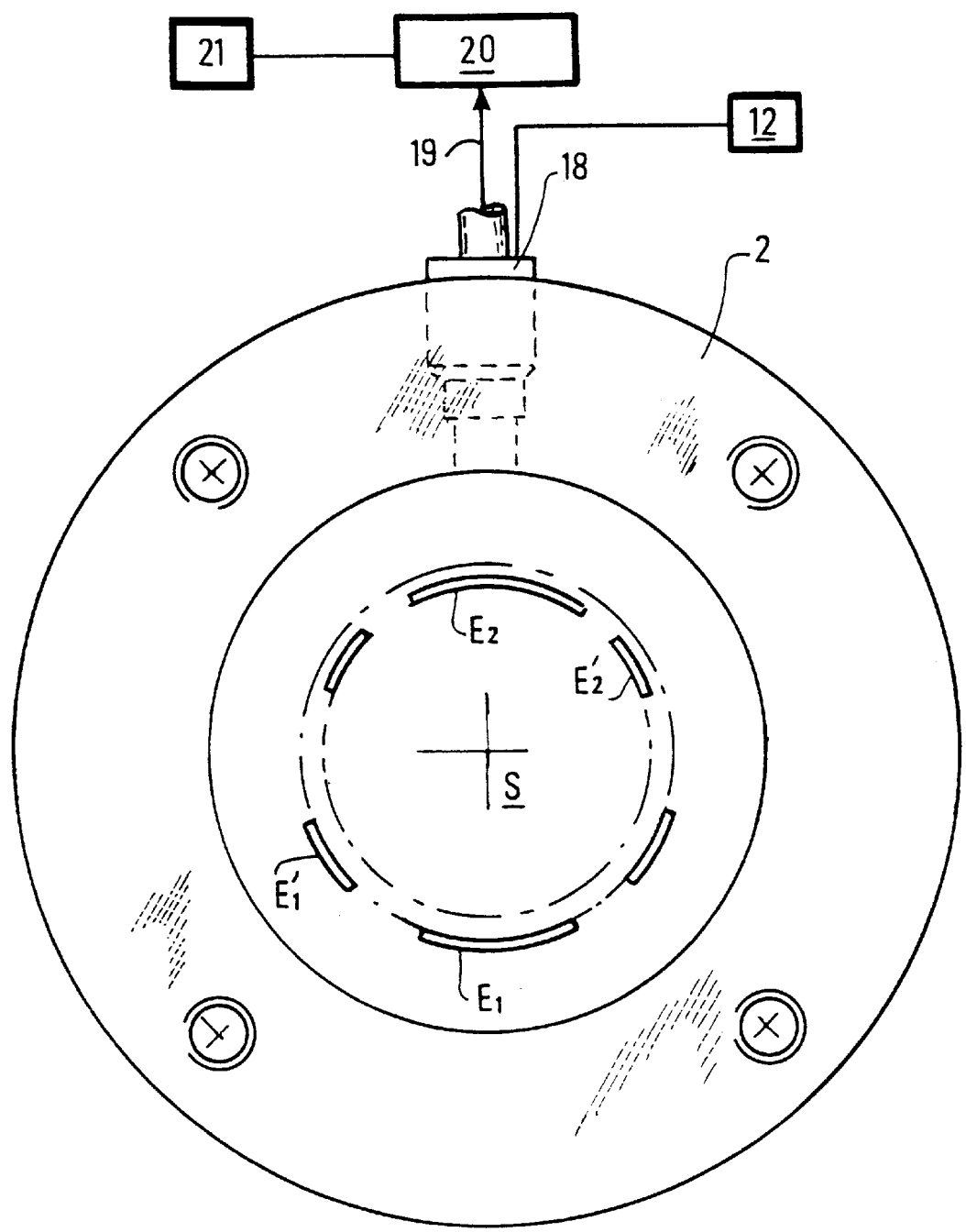

METHOD AND DEVICE FOR FAST MEASUREMENT OF THE RESISTIVITY INDEX OF SOLID SAMPLES SUCH AS ROCKS

FIELD OF THE INVENTION

The object of the invention is a method and a device for measuring the resistivity index curve of a solid sample independently of the capillary pressure curve.

Measurement of the resistivity index of small cores is necessary to obtain a precise estimation of the water saturation from log data.

BACKGROUND OF THE INVENTION

Various more or less fast and accurate methods have been proposed to measure the resistivity index of rocks. Several combinations of these techniques have been proposed. A known method for measuring the resistivity index essentially consists in combining a multicore air-water "semipermeable membrane" desaturation technique with a two-electrode resistivity measuring technique and in calculating the average saturation by weight difference. It appears that this method is very imprecise and depends too much on the handling quality; it is very slow and does not take account of a possible wettability effect.

Different solutions using the same principle have been found to improve the precision thereof with, in return, greater implementation complexity and a correlative cost increase. It is for example possible to

- carry out separate measurements on individual core samples in order to better control the capillary equilibrium and thus to obtain uniform saturation profiles,
- implement a technique using four electrodes so as to avoid overestimation of the electric resistance,
- implement a continuous injection technique in order to accelerate experiments when only curve Ir is necessary, as described for example by de Waal et al., 1991,
- optimize the duration of the desaturation process by using a micropore membrane and by reducing the length of the core samples as described by
  - Longeron D. et al., "Water-Oil Capillarity Pressure and Wettability Measurements Using Micropore Membrane Technique" SPE 30006, 1995, or
  - Fleury M. et al., "Combined Resistivity and Capillarity Pressure Measurements using Micropore Membrane Technique" Proceeding of the International Symposium of the Society of Core Analysts, Montpellier 1996.

However, when the measurement of Ir is linked with the determination of the capillary pressure curves, it is very difficult to reduce the duration of the experiments.

Other desaturation techniques such as the centrifugal method can be selected and implemented in the same way as the aforementioned "semipermeable membrane" method with multiple cores. Implementation of the centrifugal method also proved to be imprecise because of the accumulation of two important problems linked with the saturation profile and the contact resistance. On account of the known Archie relation connecting Ir and Sw (Ir=Sw$^{-n}$), the measurements are very sensitive to saturation. It is then also possible to determine the saturation profile (during a fluid injection for example) and to reduce the duration of the experiment by using a device for measuring the local saturation in situ and multiple electrodes as described by Jing et al., "Resistivity Index from non Equilibrium Measurements using Detailed in situ Saturation Monitoring", SPE 26798 Offshore European Conference 1993.

The method according to the invention allows continuous measurement of the resistivity index of a porous solid sample, combining rapidity, precision and low cost, while avoiding the drawbacks of the prior methods and notably the obligation to perform in-situ saturation monitoring, which is long and expensive.

SUMMARY OF THE INVENTION

The method according to the invention allows to rapidly and continuously obtain the variations of the resistivity index (Ir) of a porous solid sample, initially saturated by a first fluid, by means of a device comprising an elongate containment cell, means for exerting a radial pressure on the sample, electrodes pressed against the peripheral wall of the sample, allowing application of an electric current and detection of the potential differences appearing between distinct points in response to the application of the electric current, the electrodes being connected to a device for measuring the complex impedance of the sample, a first semipermeable filter permeable to the first fluid and placed substantially in contact with a first end of the sample, and pressure means for injection under pressure of a second fluid through a second end of the sample. The method is characterized in that

- it uses electrodes whose longitudinal extension is relatively great in relation to the length of the sample but shorter than this length, so selected as to involve the largest possible part of the volume of the sample in the impedance measurements while avoiding short circuits through the ends of the sample, likely to distort measurements, and
- at least one injection pressure stage is applied for the second fluid and precise continuous measurement of the complex electric impedance variations of the sample is carried out at several frequencies during a phase of displacement of the saturating fluid (drainage phase or imbibition phase), measurement being achieved without waiting for a capillary pressure equilibrium to be reached in the sample in response to each pressure stage.

Electrodes whose length ranges between ¼ and ¾ of the length of the sample and is preferably of the order of ½ of its length can be used for example.

The device according to the invention comprises an elongate containment cell, means for exerting a radial pressure on the sample, electrodes pressed against the peripheral wall of the sample, allowing application of an electric current and detection of the potential differences appearing between distinct points in response to the application of an electric current, the electrodes being connected to a device for measuring the impedance of the sample. a first semipermeable filter permeable to the first fluid and placed substantially in contact with a first end of the sample, and injection means (14) for injection under pressure of a second fluid through a second end of the sample.

The device is characterized in that the electrodes have a relatively great longitudinal extension in relation to the length of the sample (between ¼ and ¾ of the length of the sample and preferably of the order of ½ of its length) but shorter than this length, so as to involve the largest possible part of the volume of the sample in the impedance measurement while avoiding short circuits through the ends of the sample.

The method according to the invention, in relation to the prior methods, is particularly advantageous since it allows
  to draw a very precise drainage continuous resistivity index curve in a short time (about 2 days for a typical 100 mD sandstone whereas the typical time required with the continuous injection technique is often of the order of two weeks), the method is not linked with a capillary pressure equilibrium, the effect of non-uniform saturation profiles during measurement is negligible. This is due to the combination of three factors: (i) the radial resistivity measuring technique, (ii) the presence of semipermeable filters on the outlet side, (iii) all the volume of the core is analysed by means of electric measurements (this is verified when the diameter of the core is greater than its length).

BRIEF DESCRIPTION OF THE DRAWINGS

Other features and advantages of the method according to the invention will be clear from reading the description hereafter of a non limitative example, with reference to the accompanying drawings wherein FIG. 1 diagrammatically shows, in longitudinal section, a device for implementing the method, FIG. 2 shows a realization detail of a semipermeable membrane pressed against a terminal face of the sample, FIG. 3 shows the layout of the electrodes allowing to measure the resistivity index of the core.

DETAILED DESCRIPTION

Figure 4A:
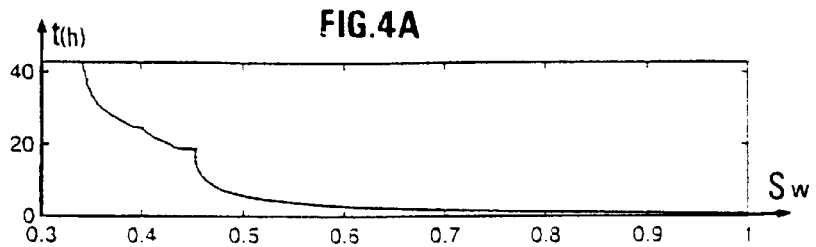
FIG. 4a shows an example of a curve describing the variation with time of the water saturation of a core of permeability 80 mD during an experiment where three pressure levels are successively applied.

The method is implemented by means of an experimental system similar to the system described in patent EP-0,701, 120 filed by the applicant.

It comprises a core containment cell comprising a hollow body 1 consisting of two symmetrically cylindrical sleeves 2, 3. They are pressed against each other by means of seals 4 and joined by screws 5. Each sleeve comprises an axial cavity for an end piece 6, 7. Sample S is placed in an annular U-shaped elastomer part forming a shell 8. The assembly consisting of sample S and shell 8 is installed in an inner cavity of sleeve 3 and is axially delimited on each side by two end pieces 6, 7. On the side of end piece 6, sample S is in contact with semipermeable filter M wettable by the first fluid (such as brine for example). Both end pieces 6, 7, whose faces opposite each other are provided with a network of grooves 9 (FIG. 2), are pressed against the sample by screwing two nuts 10 into sleeves 2, 3.

Two lines 13 run across end piece 7 and communicate the network of grooves 11 on the terminal face thereof with a first source 14 delivering the second fluid under pressure. Similarly, lines 15 run across end piece 6 and communicate the corresponding network of grooves 11 with a circuit 16 intended for recovery of the first fluid drained out of the sample as a result of the injection of the second fluid. An element 17 is installed on circuit 16 to measure the volume of fluid displaced out of sample S. A low-cost capacitive detector with a precision of 0.05 cc and a resolution of 0.01 cc, similar to the detector used in the device described in patent application FR-97/15,833 filed by the applicant, is preferably used.

The device comprises for example at least a first pair of electrodes E1, E2 cast in shell 8 so as to be closely pressed against the peripheral wall of the sample, allowing application of an electric current. By means of two other pairs of electrodes E'1, E'2 similarly cast, the potential difference created in response to the application of an electric current is measured.

This separate allocation of the pairs of electrodes, one for application of a current, the other for potential difference measurement, allows to avoid resistances due to contacts. The electrodes are for example square-shaped and made of Monel. The angular extension of a pair of electrodes around the sample is less than 90°. Their length must be less then the length of the sample between end pieces 6,7 so as to avoid electric end short circuits external to the sample, directly through the fluids, which would distort the measurements. However, their length must be great enough in relation to the length of the sample so that the current lines cover the most part of its volume with a relatively even distribution. This length can vary considerably according to the diameter of the sample. In the experiments carried out, it has been found that the length of the electrodes could advantageously range between ¼ and ¾ of the length of the sample and preferably be of the order of ½ of this length.

Through a stopper 18, the space on the periphery of shell 8 communicates with pressure means 12 allowing injection of a fluid under pressure that exerts a radial confining pressure on the sample. The radial confining pressure around the sample is for example of the order of a few MPa, sufficient to ensure proper electric contact of the electrodes. Thus, under normal conditions, the contact resistance is generally of the same order as the resistance of the sample that has to be measured with a low water saturation.

Through the stopper 18 provided with a sealed duct, conducting wires 19 linked with the various electrodes E, E' are connected to an electric conductivity measuring system 20 comprising an RLC impedance meter with four electrodes interconnected by pairs, coupled with a measurement acquisition unit 21.

RLC measuring system 20 is suited to measure the imaginary and real parts of the complex impedance of the core. It can be experimentally checked that the imaginary part (linked with the capacitive effects) is generally negligible in relation to the real part (resistance), except at high frequencies.

In order to obtain perfect sealing of the containment cell of sample S, each end piece 6, 7 comprises (FIG. 2) a groove in the terminal wall thereof for a seal 22, and a metal grate 23 coated with a plastic coating is interposed between filter M and the corresponding end piece 6. This grate is provided, on the periphery thereof, with a non-perforated ring 24 preventing the fluid from leaking by bypassing filter M.

The assembly is placed in a thermostat-controlled enclosure (not shown).

Semipermeable filter M (made of porous ceramic for example) is used here to obtain a particular saturation profile in the sample or core, as described hereafter. It also has the advantage of allowing easy determination of the average saturation and of depending only to a limited extent on the dead volumes of the end pieces. Filter M is here water wet.

Operation

Sample S, saturated with the first fluid, is placed in the enclosure and a radial confining pressure is applied through opening 18.

A second fluid such as oil is then injected through lines 13 at a first pressure and the complex impedance variations of the sample are continuously measured for several frequencies between 0.1 and some 10 MHz. The following four frequencies can be taken for example: 0.1; 1; 10 and 100 kHz, that are recorded by acquisition unit 21. The resistance R at various saturations Sw is deduced from the real part of the signal at 1kHz and the resistivity index Ir=R/Ro, where Ro is the resistance measured in the cell at a 100 % saturation, $Ro=R_{(Sw=1)}$.

Experimental results

Results

Two experiments have notably been carried out with membranes and with cores of very different perrneabilities (a 80 mD Vosges sandstone and a 2400 mD synthetic core). The fluids used are brine (20 g/l NaCl) and Soltrol 130. For the first core, three pressure levels were successively imposed (Ps=10 kPa, 20 kPa and 500 kPa), but equilibrium has been reached only with the first core, as shown by the production curve (FIG. 4a). For this type of core, the capillary pressure in the vicinity of the plateau of the curve is around 10 kPa. When the resistivity index is laid off as a function of the average saturation (FIG. 4c), it can be observed that the continuous curve obtained is in accordance with an Archie type relation throughout the saturation range covered. In the vicinity of Sw=0.45, the fact that capillary equilibrium is reached has no effect on curve Ir. The local deviation from a power law appears more clearly when the local slope n=−ln(Ir)/ln(<Sw>) is laid off as a function of saturation (FIG. 3, middle curve) n is slightly overestimated in the 0.6–0.9 range where production is very fast.

Figure 4B:
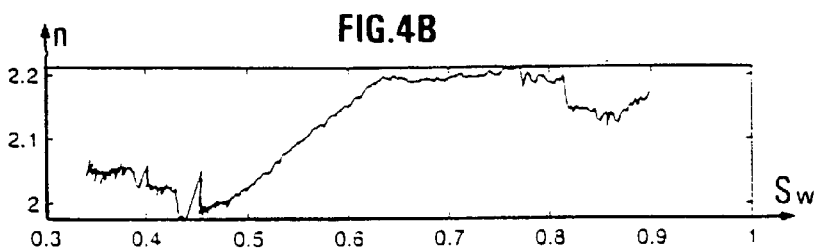
FIG. 4b shows the corresponding variation of an index $n=-\log(Ir)/\log(Sw)$.
Figure 4C:
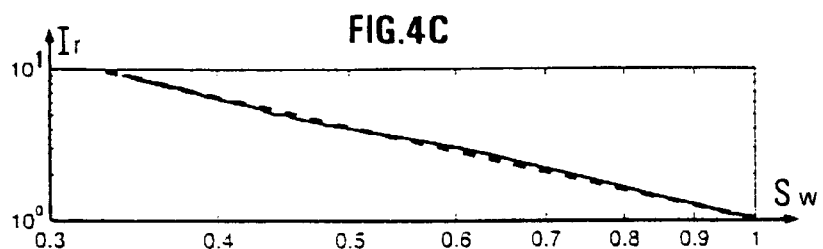
FIG. 4c shows the corresponding variation of the resistivity index as a function of the saturation variation.
Figure 5A:
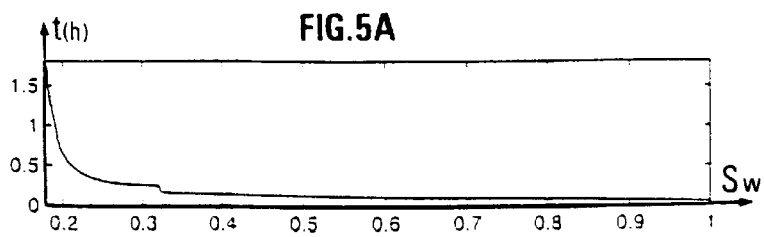
FIGS. 5a, 5b, 5c show figures respectively similar to FIGS. 4a to 4c in the case of a synthetic porous medium having a permeability of 2400 mD, obtained after approximately 2 hours, with application of a single pressure threshold of 45 kPa.
Figure 5B:
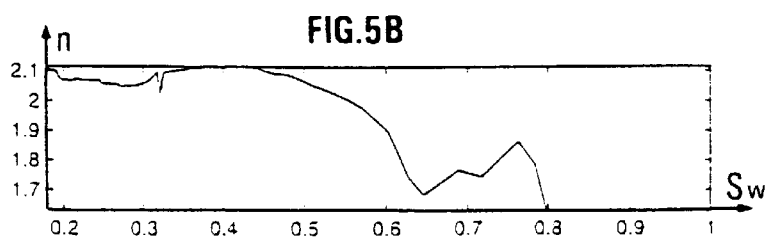
Figure 5C:
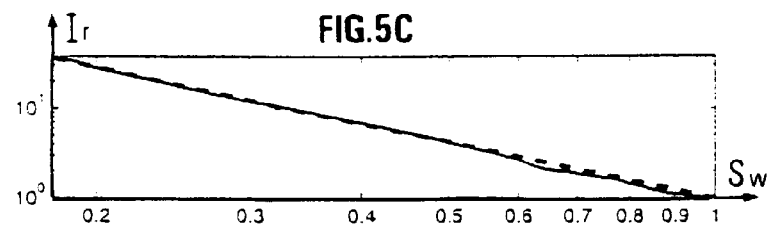

In the second example (FIGS. 5a to 5c), the experiment is much shorter (2 hours) because of the high permeability of the core. Besides, a single pressure level (Ps=45 kPa) is applied here; in relation to the previous example, Ps is much higher than the pressure around the plateau of the curve (about 3 kPa). Here again, curve Ir is well described by a power law throughout the saturation range from Sw=1 to 0.18 (FIG. 4, lower curve). The profile of the local slope (FIG. 5b) shows an underestimation of n in the high water saturation zone (Sw=0.6 to 1).

The experimental results show that resistivity index measurements can be performed in a very short time that can range from a few hours to several ten hours according to the permeability of the core, without a capillary equilibrium having to be reached. Curves Ir are determined with high precision and they are surprisingly insensitive to saturation profiles in the most part of the saturation range. A high single pressure level gives greater differences than those observed with 2 or 3 pressure levels to in the case of a high water saturation, it however allows good precision for a low water saturation.

Interpretation

Numerical simulations were carried out in order to understand the surprising insensitivity of the resistivity measurements to non-uniform saturation profiles. Two types of simulation were performed:

one-dimensional numerical simulations of "semipermeable wall" type displacement processes in order to calculate the saturation profile for a given set of capillary pressure and relative permeability curves. They have allowed to show that the relative permeability curves obtained in this type of displacement are poorly determined.

Figure 7:
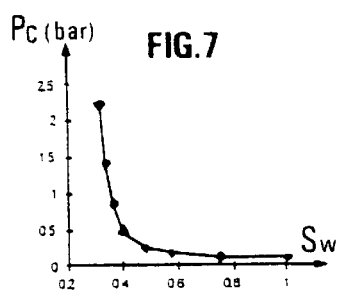
FIG. 7 shows the capillary pressure curve used in these simulations.

Three-dimensional simulations of the electric field were performed in order to reproduce the variation of the resistance between different profiles. For those shown in FIGS. 6a–6c, the following boundary conditions or parameters were imposed core permeability 100 mD;

capillary pressure obtained from measurements taken on similar cores (FIG. 7);

an arbitrary set of Corey type relative permeability curves, the indices relative to oil and water being both 3, and Kro(Swirr)=0.8;

a 0.1-mm thick water wet membrane M1 situated at z=2.5 cm (z being the direction of extension of the core) and having a permeability of 0.1 mD (typical values obtained from tests) was used;

the oil is injected at z=0 with three different pressures (16.5, 100 and 200 kPa);

saturation index n=2.

For a given saturation profile (numbered from 1 to 13), three saturation indices n=−ln (R/Ro)/ln(<Sw(z)>) are calculated np (parallel model) each point of saturation profile Sw(z) is a resistance of value $R(z)=Sw(z)^{-n}$; the average parallel resistance is $R=Rp=1/<1/R(z)>=<Sw(z)^{n}>$; this model should describe the measurements using radial electrodes;

ns (series model): the average series resistance is $R=Rs=<R(z)>=1/<Sw(z)^{-n}>$; this model should describe measurements face to face;

$n_{3D}$ (3D analog reservoir model) : the resistivity index Ir=Qo/Q, where Qo is the reference flow rate calculated for a uniform saturation Sw=1. Q is calculated for a permeability profile $K(z)=Sw(z)^n$.

Figure 6A:
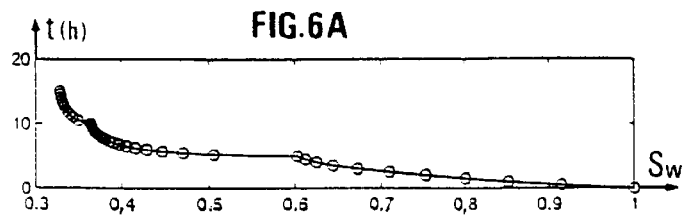
FIGS. 6a, 6b, 6c show curves obtained during numerical "Porous Plate" type displacement simulations: a production curve (FIG. 6a), a saturation profile (FIG. 6b), and three saturation indices $n_p$, $n_S$, $n_{3D}$ obtained by means of different models (FIG. 6c)
Figure 6B:
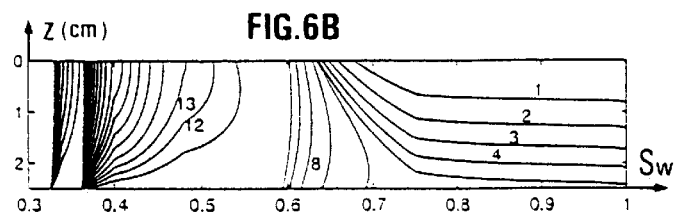
Figure 6C:
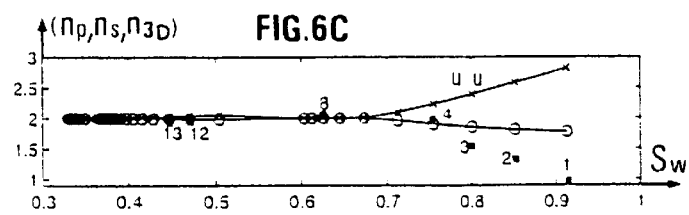
Figure 8A:
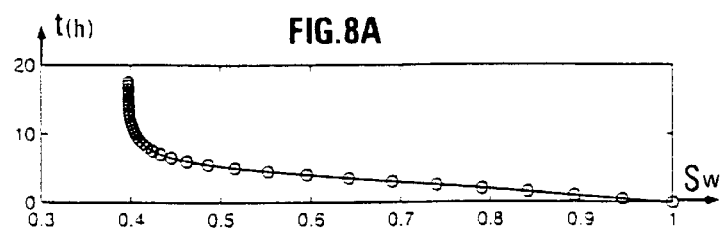
FIGS. 8a, 8b, 8c show curves similar to those of FIGS. 6a–6c in the case where a 2-mm thick ceramic filter is used instead of a membrane, with a single pressure stage of 50 kPa.
Figure 8B:
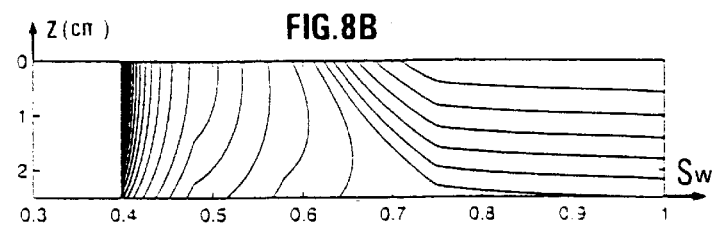
Figure 8C:
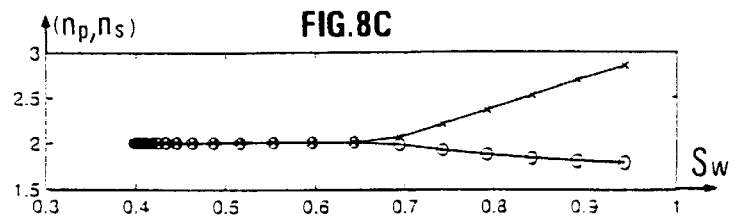

Two ranges have to be distinguished when analyzing the saturation profiles (FIGS. 6a–6c)

a high water saturation range (approximately, in the present case, Sw=0.7 to 1 where simulations show that the oil has not reached the membrane, an average and low water saturation range (Sw<0.7) where oil saturation can be higher on the outlet side (membrane side, z=2.5 cm) than on the inlet side, z=0 (saturation profile 12 for example). This effect is due to the slight pressure drop of the membrane that allows fast desaturation near the outlet and also depends on the curves Kr selected.

These simulations have allowed to conclude that:

if we compare ns, np and n3D (FIGS. 6a–6c), a resistivity measurement configuration sensitive to the parallel model is clearly less influenced by non-uniform saturation profiles. This is notably the case because of the radial geometry of the electrodes. 3D calculations show the same trend: $n_{3D}$ is very close to the input value n=2 for Sw<0.8, it is important to measure the resistance of the whole of the core; in fact, for a large number of profiles, ns and np are close because $1/<Sw(z)^{-n}>$ or $<Sw(z)^n>$ are not very different from $Sw(z)^n$, for a high water saturation (Sw >0.8), simulations show a much higher sensitivity to the saturation profiles: n3D goes from 2 to 1 (FIG. 6), a value that is far from the parallel model and contradicts the measurements. Two explanations can be accepted: (i) the electric field is greatly modified by the saturation profile and the parallel model cannot be applied; (ii) simulations do not reproduce the percolation process that appears with a high saturation Sw and fingering characteristics are more representative of the three-dimensional distribution of the oil in the porous medium; the calculated saturation profiles are therefore not pertinent.

What is claimed is:

1. A method for obtaining rapidly and continuously resistivity index (Ir) variations of a porous solid sample, initially saturated with a first fluid, by means of a device comprising an elongate containment cell (1), means (12) for exerting a radial pressure against the sample, electrodes (E1, E2) pressed against the peripheral wall of the sample, allowing application of an electric current and detection of potential differences appearing between distinct points in response to the application of an electric current, the electrodes being connected to a device (20) for measuring the impedance of the sample, a first semipermeable filter (M), permeable to the first fluid and placed substantially in contact with a first end of the sample, and means (14) for injecting under pressure a second fluid through a second end of the sample, comprising:

using electrodes with a length shorter than a length of the sample but long enough for having current lines between electrodes distributed with a relatively even distribution through the majority of the sample volume;

applying at least one injection pressure stage for the second fluid; and continuously measuring variations of the complex electric impedance of the sample at several frequencies during a phase of displacement of the saturating fluid, without waiting for a capillary pressure equilibrium to be reached in the sample in response to each pressure stage.

2. A method as claimed in claim 1, characterized in that electrodes whose length ranges between ¼ and ¾ of the length of the sample are used.

3. A method as claimed in claim 1, characterized in that electrodes whose length is of the order of ½ of the length of the sample are used.

4. A method as claimed in claim 1, characterized in that precise continuous measurements of the complex electric impedance variations of the sample are carried out at several frequencies during a drainage phase.

5. A method as claimed in claim 1, characterized in that precise continuous measurements of the complex electric impedance variations of the sample are carried out at several frequencies during an imbibition phase.

6. A device for obtaining rapidly and continuously resistivity index (Ir) variations of a porous solid sample, initially saturated with a first fluid, comprising an elongate containment cell (1), means (12) for exerting a radial pressure against the sample, electrodes (E1, E2) pressed against the peripheral wall of the sample, allowing application of an electric current and detection of potential differences appearing between distinct points in response to the application of an electric current, the electrodes being connected to a device (20) for measuring the impedance of the sample, a first semipermeable filter (M), permeable to the first fluid and placed substantially in contact with a first end of the sample, and injection means (14) for injection under pressure of a second fluid through a second end off the sample, wherein a length of the electrodes is shorter than a length of the sample but long enough for having current lines between electrodes distributed with a relatively even distribution through the majority of the sample volume.

7. A device as claimed in claim 6, characterized in that the length of the electrodes ranges between ¼ and ¾ of the length of the sample and is preferably of the order of ½ of the length of the sample.

8. A device as claimed in claim 6, characterized in that the length of the electrodes is of the order of ½ of the length of the sample.

9. A method as claimed in claim 2, characterized in that precise continuous measurements of the complex electric impedance variations of the sample are carried out at several frequencies during a drainage phase.

10. A method as claimed in claim 3, characterized in that precise continuous measurements of the complex electric impedance variations of the sample are carried out at several frequencies during a drainage phase.

11. A method as claimed in claim 2, characterized in that precise continuous measurements of the complex electric impedance variations of the sample are carried out at several frequencies during an imbibition phase.

12. A method as claimed in claim 3, characterized in that precise continuous measurements of the complex electric impedance variations of the sample are carried out at several frequencies during an imbibition phase.

13. A method as claimed in claim 4, characterized in that precise continuous measurements of the complex electric impedance variations of the sample are carried out at several frequencies during an imbibition phase.

* * * * *